(12) United States Patent
Yachia et al.

(10) Patent No.: US 6,579,230 B2
(45) Date of Patent: Jun. 17, 2003

(54) PENILE PROSTHESIS AND METHOD OF IMPLANTATION

(75) Inventors: Daniel Yachia, Herzlia-on-sea (IL); Mark Friedman, Haifa (IL); Leonid Perlin, Haifa (IL); Vladimir Gurevich, Haifa (IL)

(73) Assignee: Impetus Ltd., Haifa (IL)

( * ) Notice: Subject to any disclaimer, the term of this patent is extended or adjusted under 35 U.S.C. 154(b) by 0 days.

(21) Appl. No.: 09/882,194

(22) Filed: Jun. 15, 2001

(65) Prior Publication Data

US 2002/0193659 A1 Dec. 19, 2002

(51) Int. Cl.⁷ .............................. A61F 5/00; A61F 2/02
(52) U.S. Cl. ..................................... 600/40; 623/11.11
(58) Field of Search ................. 600/40, 30; 29/450; 604/544; 128/858; 623/11.11

(56) References Cited

U.S. PATENT DOCUMENTS

| | | | | |
|---|---|---|---|---|
| 4,060,080 A | * | 11/1977 | Akiyama | 128/858 |
| 4,267,829 A | * | 5/1981 | Burton et al. | 600/40 |
| 4,318,396 A | * | 3/1982 | Finney | 600/40 |
| 4,411,261 A | * | 10/1983 | Finney | 600/40 |
| 4,664,100 A | * | 5/1987 | Rudloff | 600/40 |
| 4,791,917 A | * | 12/1988 | Finney | 600/40 |
| 4,881,530 A | * | 11/1989 | Trick | 600/40 |
| 4,909,785 A | * | 3/1990 | Burton et al. | 604/544 |
| 5,064,434 A | * | 11/1991 | Haber | 600/30 |
| 5,553,379 A | * | 9/1996 | Westrum et al. | 29/450 |

* cited by examiner

Primary Examiner—Eric F. Winakur
(74) Attorney, Agent, or Firm—Rashida A. Karmali

(57) ABSTRACT

The present invention is a penile prosthesis device and a non-surgical method of implantation of the device into a penis. The prosthesis device is designed to be an elastic mantle to be implanted directly into the corpus cavenosum cavity. The prosthesis device contains an elongated tube plugged at both ends and fillable with a biocompatible liquid. The liquid may be pre-filled or injected into a implanted prosthesis device to achieve the resilience and feel of the penis.

The invention includes a balloon which is inserted into the corpus cavenosum cavity and a pump is used to pressurize the cavity and achieve a cylindrical expansion of the form of the penis. The invention also includes an elastic mantle having a unit including a plurality of magnets to achieve rigidity, thereby causing the penis to become erect.

27 Claims, 9 Drawing Sheets

PENILE PROSTHESIS AND METHOD OF IMPLANTATION

FIELD OF THE INVENTION

The present invention relates generally to medical prostheses, particularly to urological prostheses and methods of implantation for improved erectile function, and particularly to penile implants comprising an elastic mantle, internal elements and filling material for implanting into the corpora cavernosa, without requiring a surgical operation, and an implantation method therefore.

BACKGROUND TO THE INVENTION

Male impotence is wide spread worldwide. Some data indicate that more than thirty million people between the ages of twenty-five years and sixty years suffer from impotence in the United States alone. A number of various methods have been used to treat impotence, including pharmaceutical medicines such as Viagra or Apomorphine, natural remedies, use of external apparatus and devices to create vacuum in the penile area, implantation of prosthesis in the penile cavity called the corpora cavemosa to create an artificial erection, surgical implantation of penile prosthesis filled with solution, or implantation of a drug storage unit remote from penile tissue, but connected by a thin tubing for delivery of vasodilating drugs such as prostaglandin $E_1$, papaverine, or the like.

Several prior art patents have described penile prostheses comprising of plastic pliable elements with constant rigidity, for example, the Semirigid and Malleable Rod Penile Prostheses, located coaxially inside a silicon stem devices such as the Jonas Prosthesis, Flexirod, or the AMS-600. U.S. Pat. No. 3,987,789; U.S. Pat. No. 4,392,562; U.S. Pat. No. 4,066,073; U.S. Pat. No. 4,594,998. Disadvantageously, these types of devices are continuously rigid and cause discomfort for the patient.

Other types of penile prostheses include surgically positioned pumps for creating high pressure of liquid in the elastic silicon mantle, for example, U.S. Pat. No. 5,658,329; U.S. Pat. No. 5,803,897; U.S. Pat. No. 4,566,446; U.S. Pat. No. 4,782,826; U.S. Pat. No. 4,224,934; U.S. Pat. No. 4,235,227; U.S. Pat. No. 4,201,202; U.S. Pat. No. 4,342,308; U.S. Pat. No. 4,009,711; U.S. Pat. No. 3,853,122; U.S. Pat. No. 3,954,102; U.S. Pat. No. 5,062,417; U.S. Pat. No. 5,230,694; U.S. Pat. No. 5,167,611 or U.S. Pat. No. 4,267,829. Generally, the inflatable chambers of these prostheses are situated in the corpora cavernosa, the liquid reservoir is implanted in the inguinal area, and the pump is situated in the scrotal sac. Unfortunately, implanting these devices almost always requires implanting several components into the patient's body, for example, the reservoir with liquid, pump, several valves, connecting pipes, and the like, in addition to those components implanted directly into the penis. Therefore, the implantation of these elements requires complicated, surgical, lengthy and costly procedures to be performed. Moreover, these devices themselves are complex and expensive.

The prior art also teaches devices which use an external source of electricity and a source of alternating magnetic field changing with the frequency of 50 to 1000 Hz which influence the internal element located in the penis. This element senses the magnetic field and causes liquid in the inner reservoir to move from the reservoir into the elastic mantles located in the corpora cavernosa, and causes the penis to erect. U.S. Pat. No. 4,584,994; U.S. Pat. No. 5,427,605; U.S. Pat. No. 4,491,461 and U.S. Pat. No. 5,803,897 describes a permanent magnet which makes seesaw movements under the influence of this field. This in turn causes liquid from the reservoir to pump into the elastic mantles, thus serving as an internal element sensing alternating magnetic field of the external source.

U.S. Pat. No. 5,230,694 describes penile prostheses not containing pumps and reservoirs with a liquid, but is provided with an internal element with alternating rigidity placed in an elastic mantle which is closed by plugs at its side. The element is made in the form of a spring having coils which can be moved manually from one end of the prosthesis which is fixed to the patient's body, to its other end, thereby causing the penis to erect. The position of the spring's coils is fixed by the group of permanent magnets. These magnets are in the form of stems which are parallel to one another and are homopolarly turned to each other. The magnets' ends touching the moving spring coils are equipped with conic bulges which couple with the spring coils. Therefore, the magnets hold the spring coils by their bulges by repelling each other. However, such a construction is not sufficiently reliable. This is because it is necessary to squeeze the magnets in order to empty the erecting chambers. And since the magnets are located in the spring, it is necessary to squeeze the spring in the direction perpendicular to its longitudinal axis. The spring is highly rigid and one has to squeeze the penis strongly from the outside using one's fingers, which is a painful procedure. Moreover, the implantation of the prosthesis requires similar surgical procedures as described above for currently available penile prostheses.

Even worse, the complicated surgery may result in damage of erectile tissues and post-operative complications. Moreover, many of conventional mechanical prostheses have somewhat frequent mechanical malfunction and may require additional surgery to replace the prosthesis. Nevertheless, about twenty thousand such surgical operations are performed each year in the United States alone.

The drawbacks of the current methods of implantation and above devices are that, independently of the type of prosthesis and components used, these units are implanted into the penis by means of conventional surgical operation, by making a surgical cut in the area of the penile skin, corpora cavernosa or the scrotum for implanting the prosthesis. Such surgical operations are complex, expensive and inconvenient.

It is therefore an object of the invention to provide a non-surgical, non-intrusive penile erection device, and which reduces the pain associated with mechanical malfunction of devices.

It is also an object of the invention to provide an implantation procedure for penile prosthesis, which procedures requires no surgery, and can be carried out in an outpatient clinic.

SUMMARY OF THE INVENTION

The present invention overcomes the problems associated with previous devices and implantation methods by preferably implanting a penile prosthesis without requiring a complicated surgical procedure thereby making the procedure cost-effective and possible in an outpatient setting.

The penile prosthesis device of the present invention includes an elastic mantle in the shape of a balloon or tube, the mantle is plugged at each end and is filled with a biocompatible liquid. The prosthesis device is inserted into the cavernous cavity by means of a trocar, and requires no surgical procedure.

An additional embodiment of the invention includes a prosthesis unit having alternating rigidity and a catch for locking its position using a plurality of permanent magnets. The prosthetic device unit having the alternating rigidity comprises a thin wire, preferably made of steel, and a plurality of short discrete cylindrical elements. Each of the cylindrical elements further includes an axis hole through which passes the above-mentioned wire. The elements are coupled to each other end to end.

In another embodiment of the invention, every discrete element of the unit with alternating rigidity is made in the form of a cylinder with the alternating cut done in such a way that the outer diameter of the front of the minimal cut corresponds to the inner diameter of the front of the maximal cut.

In yet another embodiment, the discrete elements of the unit with alternating rigidity are made of ferromagnetic and non-ferromagnetic material and are located along the wire in the form of interchanging rows. One of the ends of the wire is attached to the plug at the first end of the elastic mantle. A part of the rigid pipe attached on the inner surface of the elastic mantle near its second end, is injected into the prosthesis.

In a different embodiment, the first magnet of the catch of the unit's position with alternating rigidity is attached by one of its ends or poles to the inside part of the rigid pipe. A second magnet of the catch of the unit's position with alternating rigidity and is attached by one of its ends or poles to the inside part of the rigid pipe, coaxially with the first fixed magnet, and is turned to it by its opposite end, the second end or pole of which is connected with the free end of the wire. The prosthesis is equipped with an external driver interacting with the internal catch of the unit. The external driver is made in the form of a third permanent magnet which interacts with the internal movable magnet by means of the magnetic field. The third magnet is in the form of a heavy walled pipe and an inner diameter corresponding to the size of the penis. The external driver is equipped with an element for uncoupling the third permanent magnet and the internal movable magnet.

The uncoupling element is made in the form of a ferromagnetic pipe which is inserted into the inner hole of the third magnet, and is able to move on the axis while the conjugated surfaces of the ferromagnetic pipe and the magnet are covered with a material such as Teflon, that provides a suitable drag coefficient. The uncoupling element further has the catch of position as described in detail in FIG. 6 for an uncoupling element used for two opening halves with a faster. Additionally, the elastic mantle may be equipped with an external arm made of thin non-elastic net attached at its ends to the plugs. The elastic mantle may also have a syringe activated checkvalve attached in one of the pipes. These particular characteristics in the construction of the penile prosthesis in the present invention, enable it to work reliably since the position of the unit influences the catch by means of the magnetic field of the external magnet, without deforming the penis and the internal elements of the prosthesis.

Additionally, the penile prosthesis unit with the alternating rigidity and its catch enable the prosthesis to reduce to its original state or in the non-erectile state. In this state, the prosthesis can be inserted with ease into the corpora cavernosa by a trocar like larger caliber needle, thus avoiding the need for surgical procedures involving incisions, as is the case now, when implanting a penile prosthesis.

An additional aspect of the present invention is the method of implantation of the semirigid, malleable, rod penile prosthesis and the like. For example, by implanting into the penis separately, the elastic mantle with inside elements and the filling material, using a needle-shaped catheter directly in to the penile corpora cavernosa, without making a surgical incision. Optionally, the elastic mantle may be partially pre-filled, or the filling material may be inserted into the elastic mantle already placed in the corpora cavernosa, through a needle catheter and valve. The filling material may include standard physiological solution, biocompatible elastomer, silicone, oil, or other material in liquid form. This material may cure or harden after filling. Before insertion of the elastic mantle into the corpora cavernosa the implantation method may include a step of expanding the cavity by using a high-pressure balloon, similar to angioplasty balloons.

A further benefit of the implantation method of the present invention is the minimum erectile tissue disruption created by insertion of the unfilled or partially filled elastic mantle directly into the corpora cavemosa of the penis. The elastic mantle may be filled with small diameter elements, such as malleable rods or other elements of similar diameter, through a needle-catheter approximately 2.5 to 6 mm in diameter, preferably 4 to 4.5 mm in diameter, without making a surgical incision in the penis.

After its insertion, the mantle is filled with a sufficient amount of a liquid which may or may not be self-curing. Filling the mantle is done through a valve, either by a needle catheter or by a smaller caliber needle. If a self-curing biocompatible elastomer, for example, silicone or the like, is inserted, its curing time after its injection into the elastic mantle is predetermined. The creation of the intracorporeal cavity for the elastic mantle by using a longitudinal high-pressure balloon allows the elastic mantle to reach a smooth cylindrical form upon filling with the biocompatible material.

DESCRIPTION OF THE PREFERRED EMBODIMENTS

Figure 8:
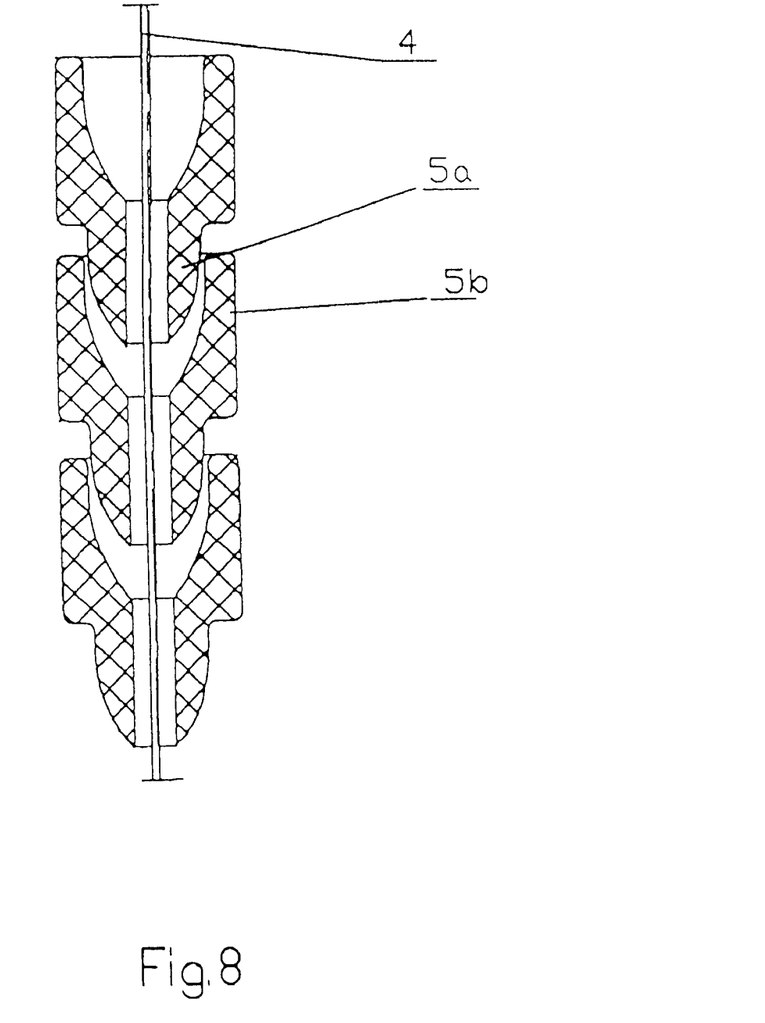
FIG. 8 presents the fragment of the unit of alternating rigidity.
Figure 9:
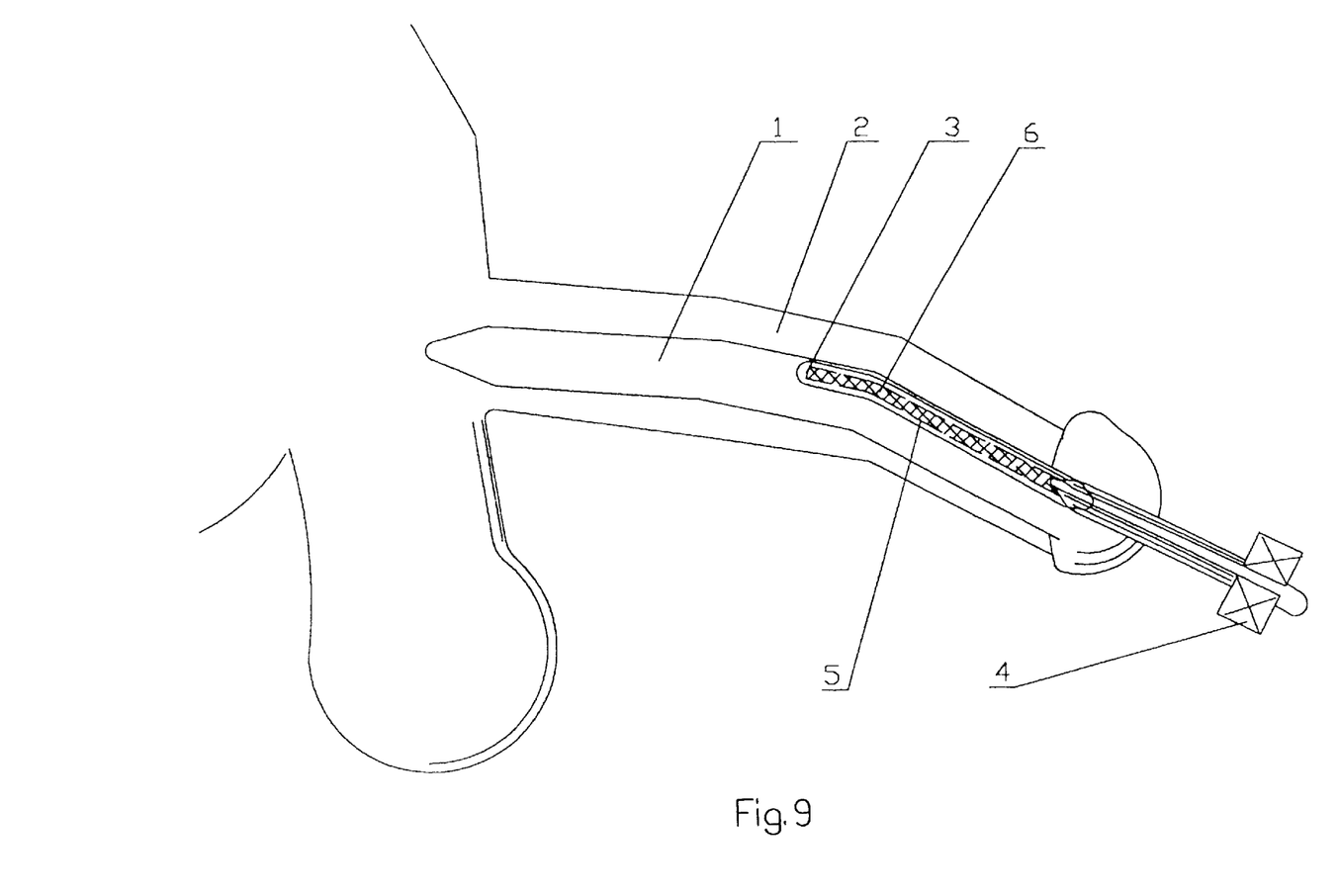
FIG. 9 illustrates the process of insertion of the unfilled (or partially filled) elastic mantle with the pre-installed malleable rod into the penis through a needle-catheter entering the tip of the corpus cavernosum.
Figure 10:
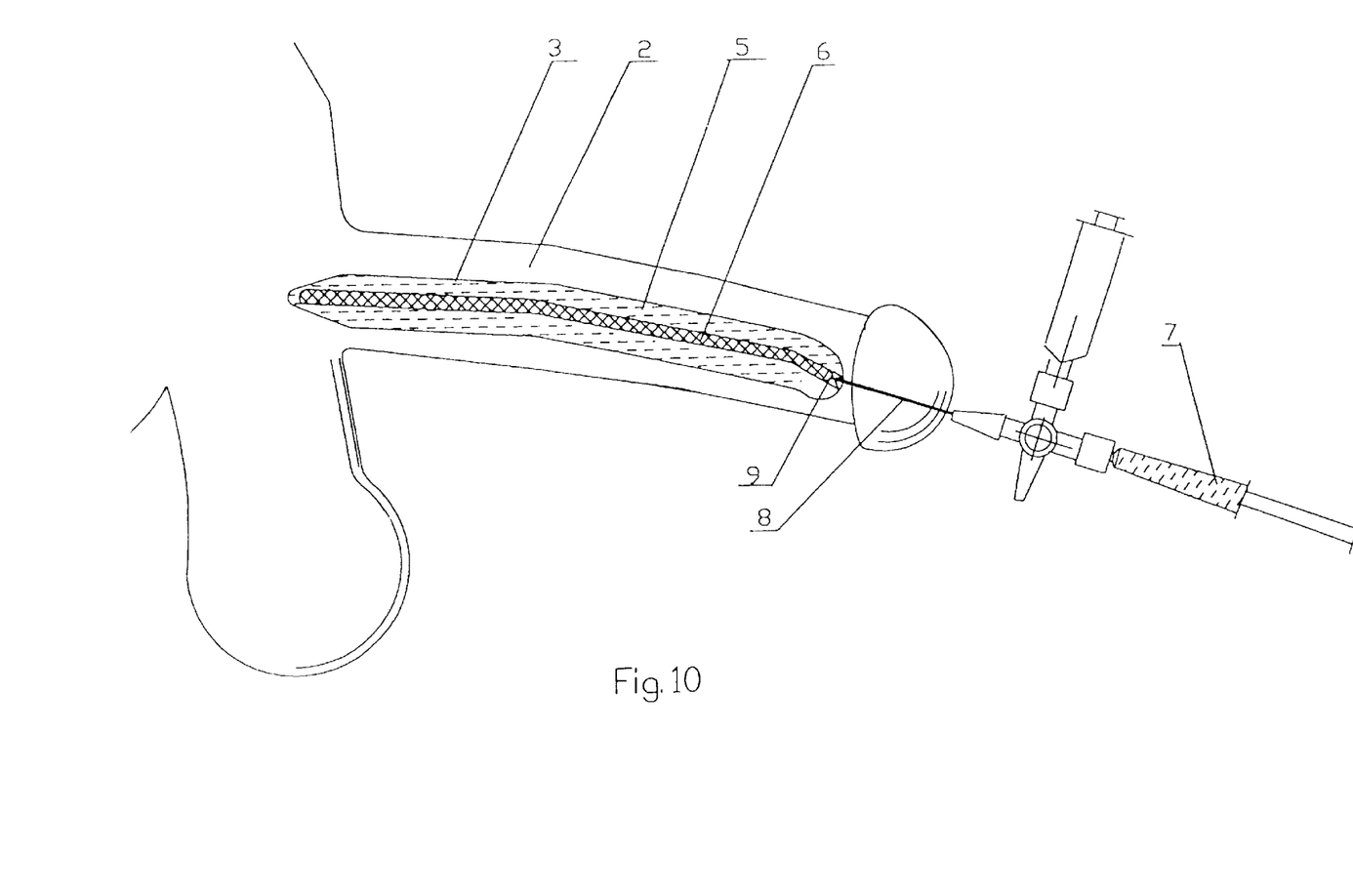
FIG. 10 shows the process of filling the elastic mantle located inside the corpus cavernosum by physiological solution or by a self-curing biocompatible liquid elastomer.

According to the invention, the Implanted Penile Prosthesis (FIG. 1) contains the elastic mantle 1 made of a biocompatible elastic material such as medical grade silicone elastomer, in the form of a pipe with plugs 2 and 3 at its ends, as well as the unit with alternating rigidity, made in the form of flexible wire 4, preferably made of medical grade stainless steel passing through the discrete elements 5 put on it. Discrete elements 5 include polyetheretherketone (PEEK) or polyetherimide (PEI). The front part of each element (5a) is conjunct with the rear part of each subsequent element (5b) (FIG. 8). These elements can have the form of short cylinders with alternating cut made in such a way that the outer diameter of the front of the less cut corresponds to the internal diameter of the front with larger cut. Beside this, the discrete elements 5 can be made of ferromagnetic (5a) and non-ferromagnetic (5b) materials located along the wire 4, in interchanging rows. Bonding elements include ultra-violet cured adhesives.

Figures 1A, 1B, 1C:
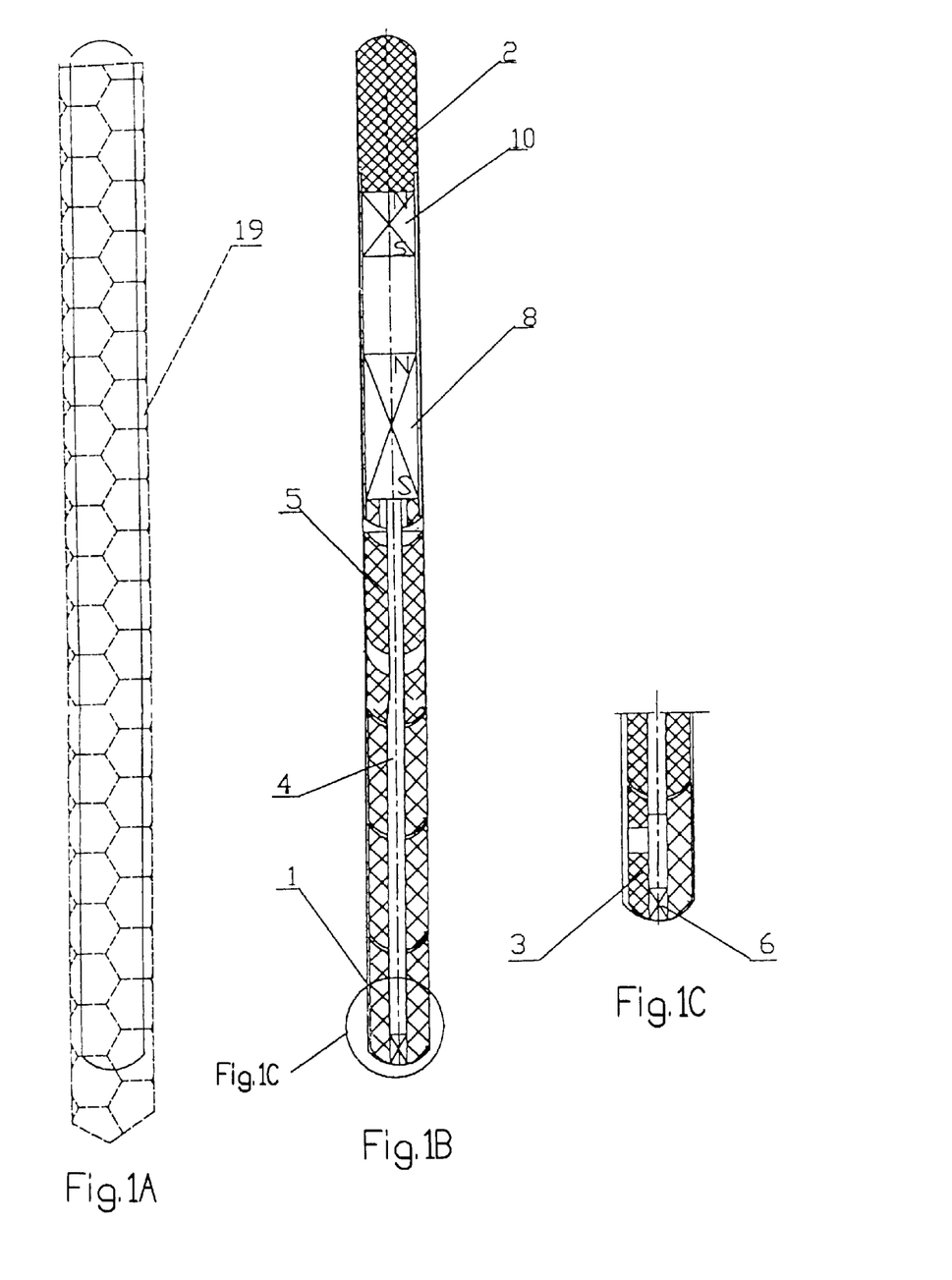
FIG. 1 presents the drawing of the implanted penile prosthesis in the condition in which it is implanted in to the penis.
Figure 3:
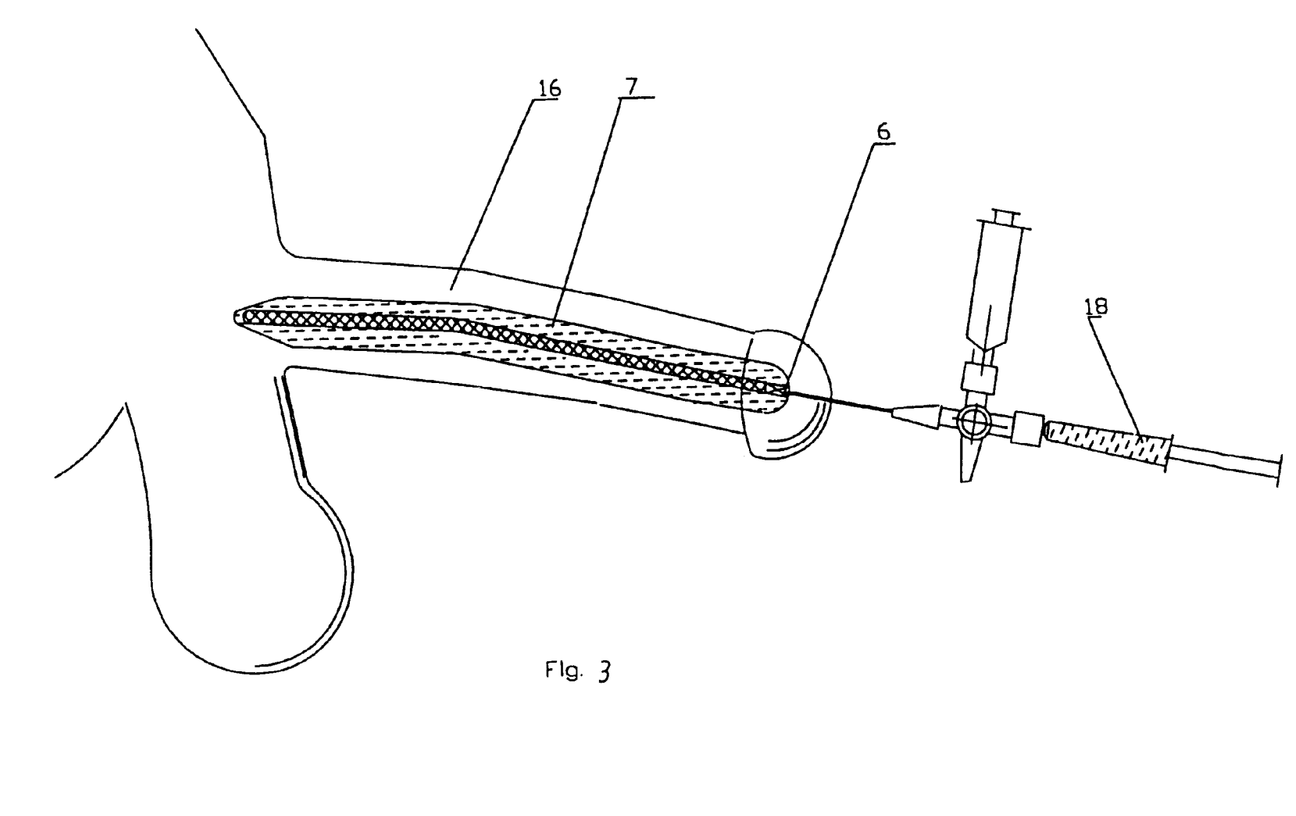
FIG. 3 shows the process of filling the implanted prosthesis by a biocompatible liquid through a valve at the distal tip of the erectile chamber.
Figure 4:
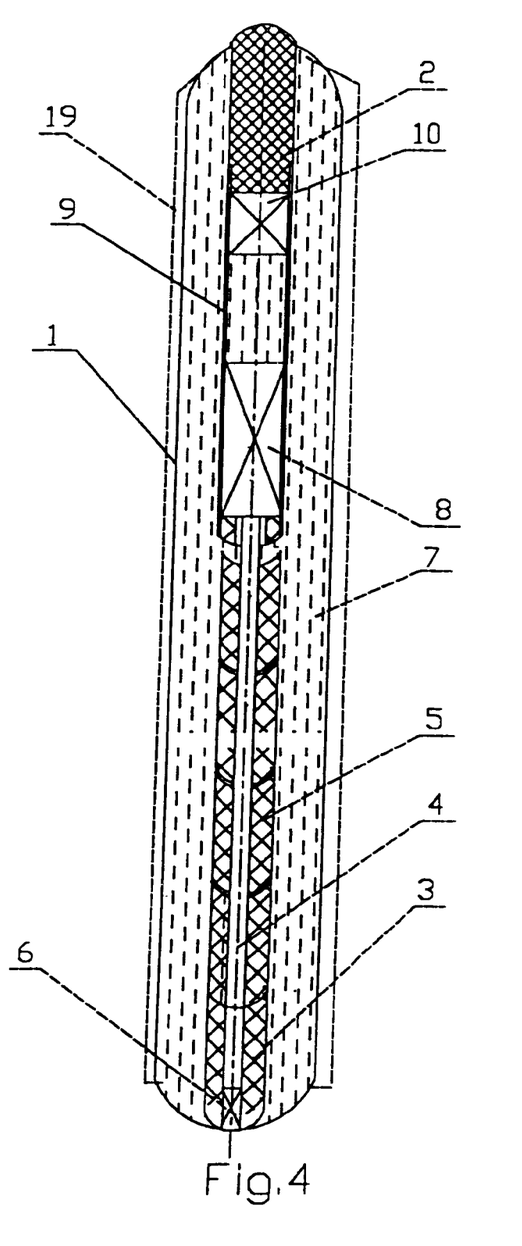
FIG. 4 shows the drawing of the prosthesis filled by abiocompatible liquid.
Figure 5:
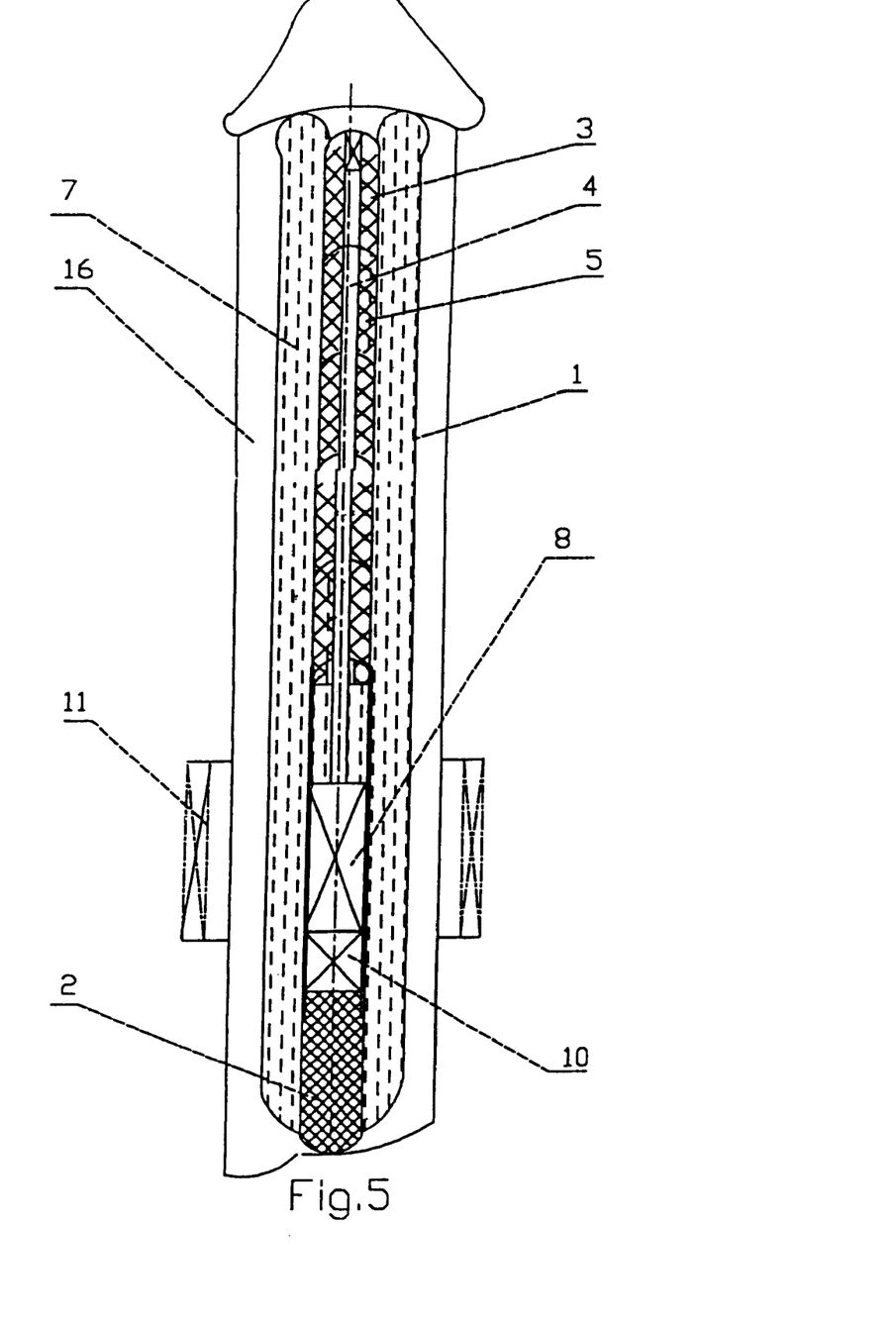
FIG. 5 shows the drawing of the prosthesis implanted into the penis, with the magnet put onto penis influencing the catch of the position of the element with alternating rigidity. The element with permanent rigidity is in the condition of the maximal rigidity, while the penis is erected.

Plug 3 has a syringe activated checkvalve 6 for filling through it the mantle 1 by a biocompatible liquid 7 (FIG. 3). One end of the flexible wire is fixed to the distal plug 3, the other end is connected with movable magnet 8. This magnet can be moved in a piece of the a rigid pipe 9 attached to the plug 2. It is directed toward the movable magnet 8 by its inverse pole and is fixed to the end of the rigid pipe 9 (FIG. 4). The device has also an external driver 8. This driver is made in the form a permanent magnet 11 (FIG. 6), in the form of a cylinder. The internal diameter of the magnet 11 is chosen in such a way that the magnet can be freely put around and removed from the penis after an of erection is achieved (FIG. 1). Magnet 11 is equipped by the uncoupling element with the movable magnet 8 providing changes of magnetic connection between them. This can be provided by means of making magnet 11 in the form of two detachable halves provided with a lock 12 (FIG. 6), or by means of an additional ferromagnetic shield 13 (FIG. 7) of cylindrical form, which can be moved coaxially in magnet 11 and is provided with a lock 14. The permanent magnets comprise of a metal alloy Nd-Fe-B coating with parylene.

Figure 2:
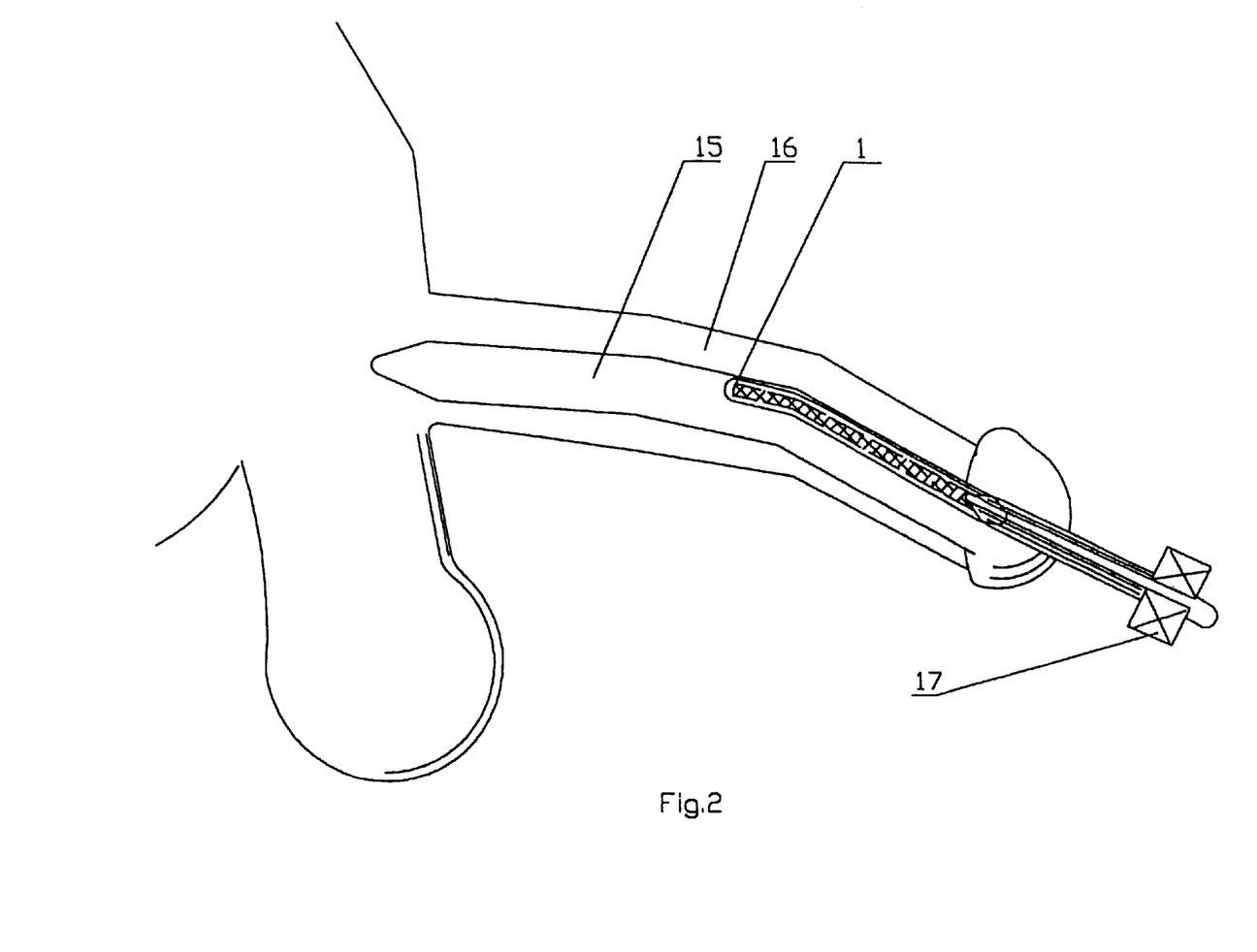
FIG. 2 shows the process of implantation of the prosthesis into the penis through a trocar.

The Implantable Penile Prosthesis is inserted into the corpora cavernosa 15 of the penis 16 through a trocar 17 (FIG. 2) in the state when the elastic mantle 1 is not filled with the biocompatible liquid. After implantation of the prosthesis into the corpora cavernosa, the elastic mantle 1 is vacuumed, and further is filled with the biocompatible liquid by means of the injector 18. The elastic mantle 1 gets larger in its size and fills the cavity of corpora cavernosa. Since this cavity can be of irregular form, the elastic mantle 1 can be provided with the external non-elastic arm 19 made in the form of the net or mantle freely put in the initial position on the elastic mantle 1 and attached to its both sides are plugs 2 and 3. The non-elastic arm comprises of an ultra thin polyester tubing or net. The arm can be freely expanded together with the elastic mantle reaching the maximal diameter of corpora cavernosa. Then it prevents the elastic mantle from further deformation keeping its cylindrical form.

In flaccid penile position, the magnets do not touch one another and wire 4 with the discrete elements 5 is in its free state (FIG. 4).

Figure 6:
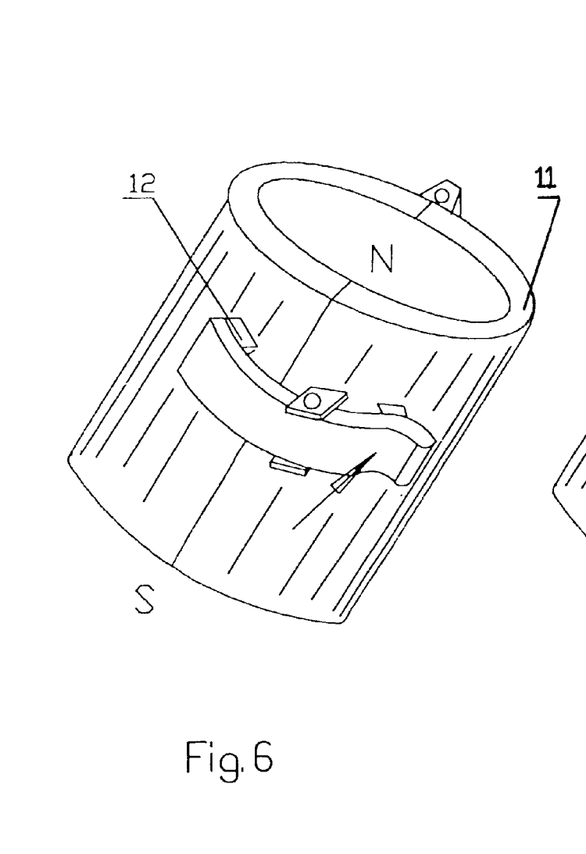
FIG. 6 shows the construction of the external magnet consisting of two opening halves.
Figure 7:
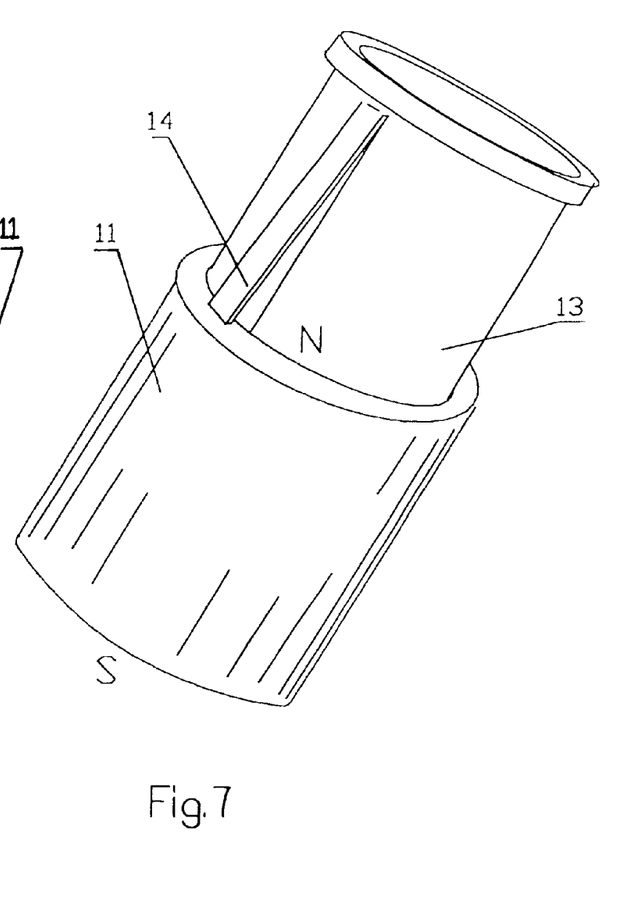
FIG. 7 shows the construction of the external magnet provided with the collapsible magnetic shield and the lock.

In order to create an erection, it is necessary to put the external magnet 11 next to the penis in the position illustrated in FIG. 6 or 7. The magnet should be moved in the direction of the body. By means of the magnetic field, magnet 11 gets coupled with the movable magnet 8 causing it to move synchronically in the pipe 9, till it touches the immovable magnet 10. While moving, the magnet 8 tightens the wire 4 with the discrete elements 5, and also pulls together the fronts of the elastic mantle 1. The discrete elements move toward search other until their conjugated surfaces meet, thus forming a rigid construction. The general rigidity of the prosthesis sufficiently grows, and the penis becomes erected. The state of magnet 8 (and consecutively of the entire prosthesis) is fixed due to attraction of magnets 8 and 10. After that, the magnetic connection of the external magnet 11 with the movable magnet 8 is interrupted by meads id uncoupling the magnet's halves (FIG. 7). Then the remove magnet 11 is removed from the penis. To get into the initial flaccid states, it is necessary to put the remote magnet 11 on the penis, to restore connection between magnet 11 and the movable magnet 8, and to move magnet 11 towards the penis's end, drawing the movable magnet 8m as well as the ferromagnetic discrete elements 5, which one by one are get out of coupling with non-ferromagnetic elements. In this case, all elements of the construction are returned into their initial state, providing for returning the penis to the flaccid position.

The described construction provides a reliable functioning of the penile prosthesis and makes the conventional surgical implantation unnecessary, thus resulting in a simpler and less costly process of implantation.

According to the method of the present invention, the elastic balloon (which can be supplied with reinforced walls) pre-determining its inflated shape 3 usually made of silicone elastomer or other biocompatible material with some physical properties (FIG. 1) is inserted into corpora caverosa 1 of the penis 2 through a needle-catheter 4. In its insertion the balloon 3 can be empty or partially filled by a physiological solution 5, or by a self-curing biocompatible liquid material mixture (as silicone, for example). Semirigid or malleable rods 6 or other elements of the construction can be pre-installed into the balloon 3.

After inserting the balloon 3 into the corpora cavernosa, it is completely filled (FIG. 2) by the physiological solution 5 or by a self-curing biocompatible liquid material mixture. The balloon can be filled by means of the syringe 7 through a needle 8 inserted through a valve 9.

If the balloon is filled with a physiological solution, after retrieval of the injection needle the prosthesis will mimic a natural erection. If a self-curing biocompatible liquid material with predetermined curing time is injected, after solidification of the material the prosthesis will mimic a natural erection.

In order to allow an even and cylindrical expansion of the balloons, before their insertion into the corpora cavernosa, the corporal cavities can be expanded by using a high pressure balloon (similar to angioplasty balloons) inserted into the corpora cavernosa through the above mentioned needle catheter. The pre-creation of the intra-corporeal cavity to host the elastic mantle by using a longitudinal high-pressure balloon allows to fill the elastic mantle and obtain a smooth cylindrical form prosthesis.

The described method of the prosthesis's implantation enables to avoid surgical incisions to the penile tissues, thus reducing the cost of the implantation and diminishing the risk of post-operative complications.

What is claimed is:
1. A penile prosthesis device comprising;
an elastic mantle shaped in the form of an elongated tube,
said tube having a suitable length,
said tube having a first and second end, said first and second ends having plugs inserted therein, wherein one of the plugs includes a syringe activated check valve.

2. The penile prosthesis device according to claim 1, wherein said mantle includes a biocompatible liquid and is adapted to be placed in a trocar needle and implanted into the corpora cavernosa without requiring a surgical procedure.

3. The penile prosthesis device according to claim 1, wherein the elastic mantle is provided with an external arm, said external arm being made of material including a third non-elastic net or a third mantle having a first and a second end attached to the plugs of the first and second ends of the tube.

4. The penile prosthesis device according to claim 1 further including a reservoir means interconnected via a fluid delivery means for conducing the liquid from the reservoir means to the implanted mantle.

5. The penile prosthesis device according to claim 4, wherein said reservoir means and the liquid delivery means are configured to define an integral unit.

6. The penile prosthesis device according to claim 1, wherein a biocompatible liquid includes silicon, physiologically saline oil or curable fluid approximating the feel of a human penis.

7. A method of implanting a penile prosthesis device, according to claim 1, without requiring surgical procedure, said method comprising the steps of:
placing an elastic mantle filled with a biocompatible liquid into a trocar, inserting a needle-catheter portion of the trocar on an aseptic portion of a human penis, to reach a penile corpora cavernosa implanting the elastic mantle into the corpora cavernosa cavity, and removing the needle-catheter portion from a penis, without loss of the biocompatible liquid.

8. The method according to claim 7, further comprising the step of delivering a biocompatible liquid into the implanted elastic mantle to achieve the resilience human penis.

9. The method according to claim 7, wherein the implanted elastic mantle includes a malleable rod filled with a biocompatible material, said method comprising the step of:
implanting directly into the corpora cavernosa a pre-filled elastic mantle, and occluding an aperture created by the needle in the elastic mantle during filling of the biocompatible material.

10. The method according to claim 7 further comprising the steps of:
inserting into the corpora cavernosa a compressible balloon using a trocar needle and delivering pressure into said balloon to expand the cylindrical form of a human penis before implanting the elastic mantle.

11. A penile prosthesis comprising;
an elastic mantle in the shape of a tube or balloon and having a suitable length,
said tube having a first and second end and each of the first and second end having a plug inserted therein,
one of the ends of said tube having a plug containing a syringe activated check valve,
a unit of alternating rigidity located in said mantle, said unit having a lock whose position is determined using a permanent magnet.

12. The penile prosthesis device according to claim 11, wherein the unit of alternating rigidity comprises a thin wire, having a first and second end, said wire consisting of steel, one end of said wire being attached to the plug at a front of the elastic mantle,
a plurality of short, discrete cylindrical elements each having a front part and a rear part, each having a passage means at the axis through which passes the thin wire, wherein the front part of an element is coupled to the rear part of a succeeding element along the length of the elastic mantle, and an external driver means to create a magnetic force.

13. The penile prosthesis device according to claim 11, wherein discrete elements of the unit with alternating rigidity have a cylindrical form having an external diameter and an internal diameter, said external diameter of an element having a small cut corresponding to the internal diameter of an element having a large cut.

14. The penile prosthesis device according to claim 11, wherein discrete elements of the unit with alternating rigidity comprises ferromagnetic or nonferromagnetic material and said elements are located along the wire in the form of interchanging rows.

15. The penile prosthesis device according to claim 11, wherein the elastic mantle has an internal surface and attached to this internal surface at the first end of the elastic mantle is a piece of pipe, wherein magnets work as a catch for the unit of alternating rigidity.

16. The penile prosthesis device according to claim 15, wherein the first magnet of the catch of the unit with alternating rigidity, said magnet having a first end and a second end, said first and second ends being attached to the inside of the pipe.

17. The penile prosthesis device according to claim 16, wherein the second magnet of the catch of the unit with alternating rigidity, said magnet being movable inside the pipe, said magnet being installed coaxially with a first immovable magnet, having a first pole and a second pole, and said magnet being adversely positioned in relation to a first pole, with the second pole being connected to a free end of a wire.

18. The penile prosthesis device according to claim 11, further provided with an external driver, said external driver interacting with the unit with the alternating rigidity via an internal catch.

19. The penile prosthesis device according to claim 18, wherein the external driver comprises a third magnet, said third magnet interacting with an internal magnet via the magnetic field.

20. The penile prosthesis device according to claim 19, further comprising a fourth permanent magnet in the form of a thick-walled pipe, said fourth permanent magnet having a diameter corresponding to the diameter of a penis, said fourth magnet having a property of coupling with the internal magnet.

21. The penile prosthesis device according to claim 20, further including an external driver is provided with an element, said element having a property of uncoupling the fourth permanent magnet from the internal magnet.

22. The penile prosthesis device according to claim 20, wherein the coupling element is provided with a positioning lock.

23. The penile prosthesis device according to claim 11, wherein the elastic mantle is provided with an external arm, said external arm being made of material including a thin non-elastic net or a thin mantle having a first and a second end attached to the plugs of the first and second ends of the tube.

24. A penile prosthesis device kit comprising;

an implantable elastic mantle, at least one trocar needle attachable to a fluid delivery means, a reservoir means containing a biocompatible liquid, said fluid delivery means and said reservoir means configured to allow delivery of the biocompatible liquid to the implantable elastic mantle, at least two plugs for inserting at each end of the implantable elastic mantle, wherein one of the plugs contains a syringe activated check valve, and a plurality of aseptic or alcohol swaps.

25. The penile prosthesis device kit according to claim 24, further comprising a unit of alternating rigidity located in said mantle.

26. The penile prosthesis device kit according to claim 24, further comprising a balloon adapted to apply pressure and expand the cylindrical form of a penis.

27. The penile prosthesis device kit according to claim 21, further comprising an external driver means to create a magnetic force and guide the unit with alternating rigidity.

* * * * *